United States Patent [19]
Markle et al.

[11] Patent Number: 5,262,037
[45] Date of Patent: Nov. 16, 1993

[54] ELECTROCHEMICAL SENSOR

[75] Inventors: David R. Markle, Paoli, Pa.; Stuart P. Hendry, Aylesbury, England

[73] Assignee: Biomedical Sensors, Ltd., High Wycombe, England

[21] Appl. No.: 887,615

[22] Filed: May 22, 1992

[51] Int. Cl.$^5$ ............................................. G01N 27/26
[52] U.S. Cl. .................... 204/415; 204/403; 128/635
[58] Field of Search ............... 128/635, 637, 639, 657, 128/658; 204/415, 403

[56] References Cited

U.S. PATENT DOCUMENTS 3,905,888  9/1975  Mindt et al. ................... 204/415
5,166,990  11/1992  Riccitelli et al. ............... 128/637

Primary Examiner—John Niebling
Assistant Examiner—Bruce F. Bell
Attorney, Agent, or Firm—Peter C. Richardson; Lawrence C. Akers; Mark Dryer

[57] ABSTRACT

An electrochemical sensor for the determination of the partial pressure of oxygen in a bloodstream comprising a cathode and an anode immersed in an electrolyte contained in a chamber defined by an oxygen gas permeable membrane wherein the conductor forming the anode is folded into a "U" shape so that the exposed distal end surface thereof faces the distal end surface of the cathode.

7 Claims, 2 Drawing Sheets

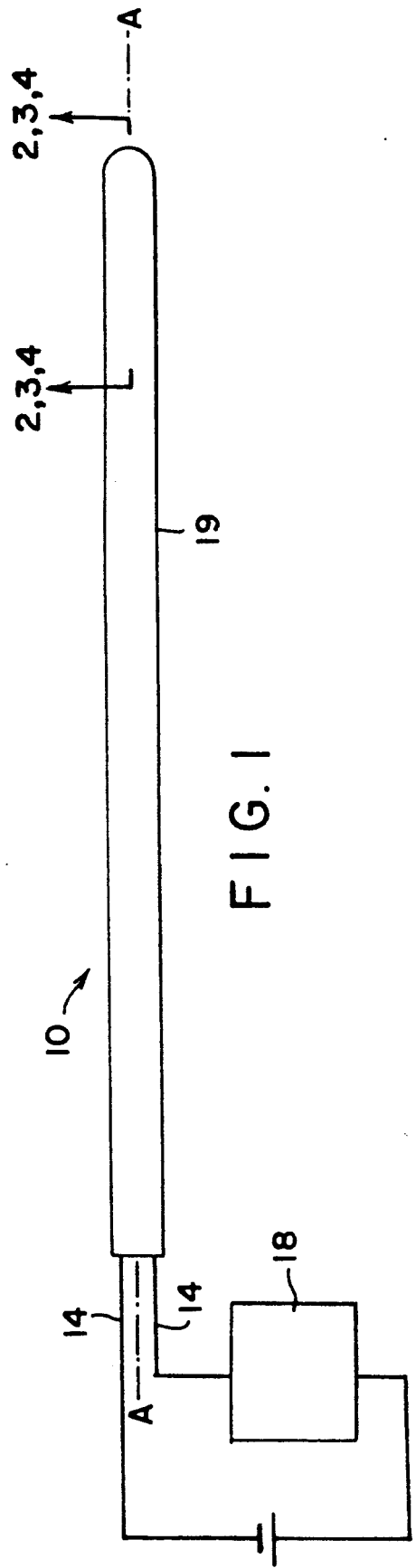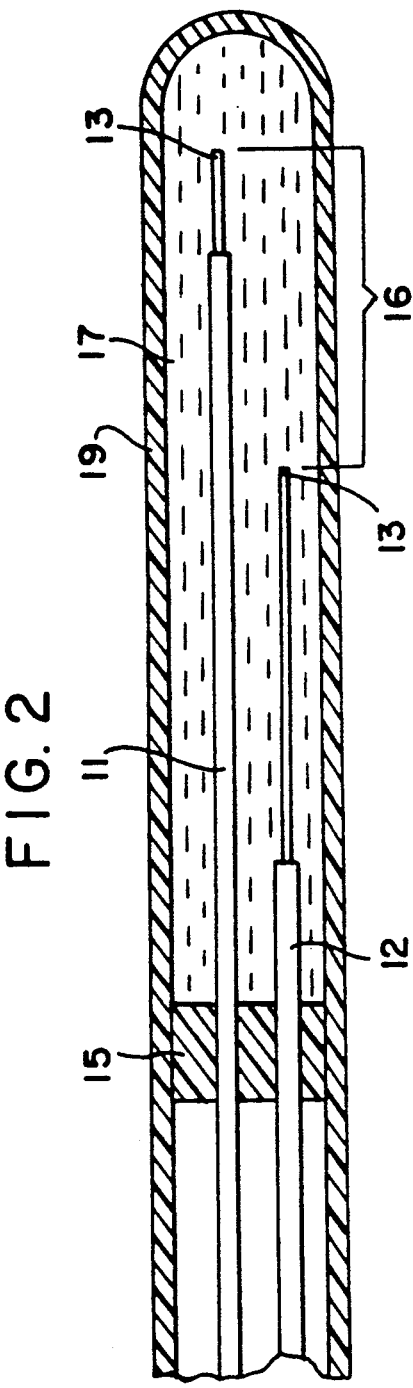

ELECTROCHEMICAL SENSOR

FIELD OF THE INVENTION

This invention relates to an electrochemical sensor. More particularly, a electrochemical cell structure that prevents rapid failure of the conductors therein.

BACKGROUND OF THE DISCLOSURE

U.S. Pat. No. 3,905,888 discloses one particular oxygen sensor for use in vivo in the vasculature of a human or animal. The disclosure of the '888 patent is hereby incorporated by reference and made a part of the background of this disclosure. The anode is typically longer and made of silver. The cathode is shorter and made of a noble metal, such as gold, platinum or silver. The anode and cathode are immersed in an electrolyte, an appropriate potential is applied therebetween and a current flow between them is monitored as an indication of oxygen content in the electrolyte. If holes exist in the insulation of the cathode, dendrites will grow through the hole to the anode and short out the sensor. To avoid that problem another approach has been tried. Specifically, the length over which an uninsulated portion is next to an insulated part is minimized. That geometric arrangement is prone to earlier failure because the metal consumed tends to be at the base of the anode near the distal end of the insulation. Specifically, that is the site for the short path for flow of current between the anode and the cathode. After a short while the tip of the anode becomes separated from its insulated base once the silver thereat has been consumed.

The need to provide a longer lived and more reliable design for the conductors in an electrochemical cell is not fulfilled by the '888 patent.

SUMMARY OF THE INVENTION

An electrical circuit includes a plurality of elongate insulated conductors each having an exposed uninsulated distal end surface and a proximal end. The distal surface of each is preferably substantially normal to its elongate insulated conductors. A support associated with the plurality of elongate insulated conductors positions each conductor with the uninsulated distal end surface thereof in generally facing relation to the distal end surfaces of one or more other elongate insulated conductors.

A gap between the facing distal end surfaces of the elongate insulated conductors defines approximately equal distances between the facing distal end surfaces. An electrolyte, such as a buffered potassium chloride solution disposed within the gap permits flow of electrical energy across the gap and between the distal end surfaces. A current sensitive measuring device in circuit with a power source between the proximal ends of the elongate insulated conductors monitors changes in the flow of energy at the distal end surfaces.

The electrical circuit most preferably has two conductors in the plurality. The facing distal end surfaces may be substantially parallel to each other, although this is not required. An electrochemical cell preferably results from the conductors, the electrolyte in the gap and the current sensitive measuring device in circuit with a power source. The electrochemical cell is an oxygen sensitive device generating a current flow between one conductor, that is an anode and another conductor, that is a cathode. The current is measurable at the proximal ends.

The electrolyte is most preferably contained within a gas permeable membrane that permits oxygen to diffuse therethrough and the cathode is an insulated noble metal preferably silver wire and the anode is an insulated silver and/or silver chloride wire. Each wire is stripped of insulation near its respective distal end surfaces. The membrane may be sized to fit within a catheter of a diameter and length capable of being inserted into the vasculature of a human or animal. The stripped cathode may have a shorter length than the length of the stripped anode. The elongate anode is preferably supported parallel to the elongate cathode and the anode is folded near the transition between the stripped portion and insulated part. There the anoded is folded into a "U" shape such that the distal end surface thereof faces the distal end of the cathode.

A method for manufacturing an electrochemical sensor may have an anode and a cathode beginning with the step of folding near the transition between the stripped portion and insulated part of the anode into a "U" shape so that an uninsulated distal end surface thereof faces in the direction of the proximal end thereof. The second step may be positioning the cathode adjacent the insulated part of the anode with the uninsulated distal end surface of the cathode facing the distal end surface of the anode with a gap therebetween. Placing the positioned cathode and the facing anode within a gas permeable membrane tube with the anode and cathode parallel to an axis of the gas permeable membrane tube can be the next step. Sealing the insulated parts of the anode and cathode proximal to the gap provides an electrochemical cell chamber within the gas permeable membrane. Filling the gas permeable membrane tube with electrolyte to surround the facing distal end surface is a further step. Closing the distal end of the gas permeable membrane completes the electrochemical cell.

BRIEF DESCRIPTION OF THE DRAWINGS

FIG. 1 is a perspective and schematic view of an electrical circuit.

FIG. 2 is an enlarged side view in (partial) cross section of an oxygen sensor such as in FIG. 1 as would be seen if the cross section were taken along line 2—2 in FIG. 1. The sensor in FIG. 2 is like that disclosed in U.S. Pat. No. 3,905,888.

DETAILED DESCRIPTION OF THE INVENTION

Figure 3:
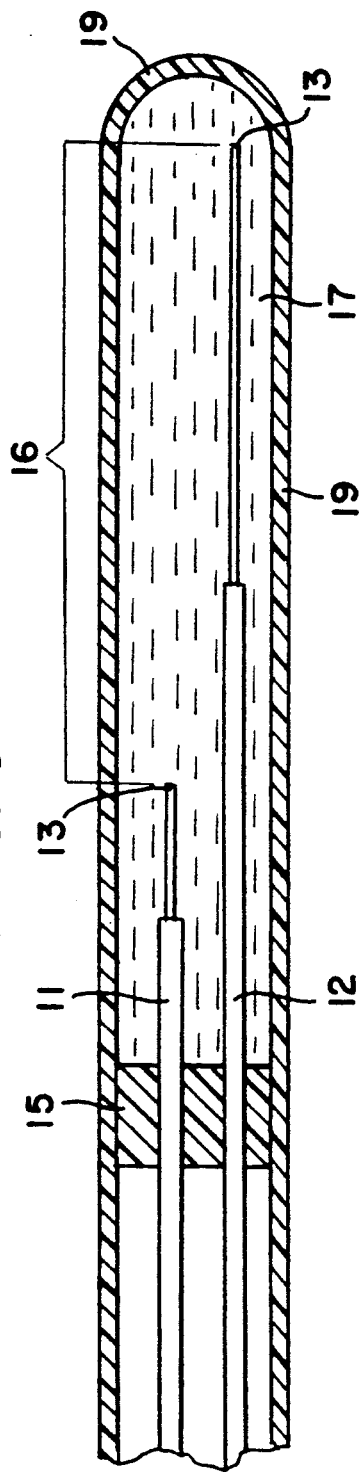
FIG. 3 is an enlarged side view in (partial) cross section of an oxygen sensor, such as in FIG. 1 as would be seen if the cross section were taken along line 3—3 in FIG. 1. The sensor in FIG. 3 is an approach to resolve the difficulties of the arrangement in FIG. 1.

An electrical circuit 10 and method of manufacture are disclosed and claimed. The claims are not limited to the particular electrical circuit 10 for a blood gas sensor described as a preferred embodiment described and illustrated by way of example and the methods of manufacture specifically explained. The claims are to be considered in view of the existing knowledge of skilled artisans in the Field and prior to the inventions defined by the language of the claims herein as amended or considered in view of knowledge of skilled artisans prior to these inventions.

The electrical circuit 10 is in the preferred embodiment a blood gas sensor for placement in the vasculature of a human or animal and so is of a diameter sufficiently small so as to be able to be placed by insertion through a catheter in the blood vessel such as an artery. The electric circuit 10 includes a plurality of elongate insulated conductors 11 and 12 each having an exposed uninsulated distal end surface 13 and a proximal end 14, shown in FIGS. 2, 3, and 4. The conductors, 11 and 12 are in the preferred arrangement thin wires made of silver for the cathode and silver and/or silver chloride for the anode with polyester insulation but the disclosure should not be limited to those materials as the particular gas to be measured may require a different electrochemical cell, gas permeable membrane, potential, geometry, chemistry or wire insulation. The preferred embodiment is selected to measure the partial pressure of oxygen entrained in the blood stream. Therefore, an in vivo blood gas sensor for the partial pressure of $O_2$ is disclosed. The distal surface 13 of each conductor 11 or 12 is preferably substantially normal to its elongate insulated conductor wire. A support 15 associated with the plurality of elongate insulated conductors 11 or 12 positions each conductor 11 or 12 with its uninsulated distal end surface 13 in generally facing relation to the distal end surfaces 13 of one or more other elongate insulated conductors 11 or 12.

A gap 16 between the facing distal end surfaces 13 of the elongate insulated conductor wires defines approximately equal distances between the facing distal end surfaces. An electrolyte 17 is disposed within the gap 16 so that the electrochemistry permits flow of electrical energy across the gap 16 and between the distal end surfaces 13 as a function of the amount of in vivo entrained gas, i.e. oxygen. The electrolyte 17 is a buffered potassium chloride solution. A current sensitive measuring device in circuit with a power source 18 in FIG. 1 for example, an ampere meter and a battery between the uninsulated proximal ends of the elongate insulated conductors 11 and 12. Specifically, the proximal end of the anode connects to the positive terminal of the battery in a manner well known. The ampere meter thus, monitors changes in the flow of energy through the electrolyte 17 between the distal end surfaces 13.

Figure 4:
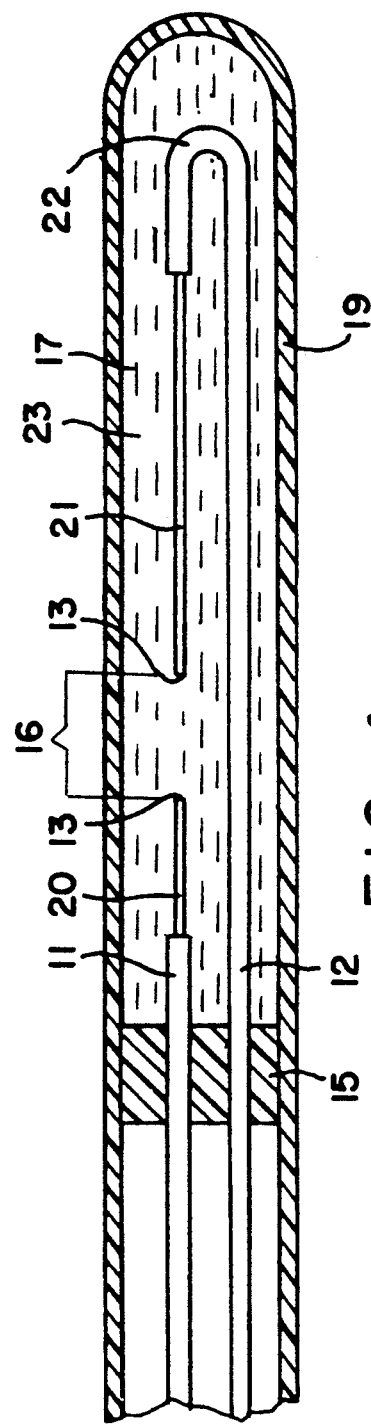
FIG. 4 is an enlarged side view in (partial) cross section of an oxygen sensor, such as in FIG. 1, but as would be seen if the cross section were taken along line 4—4 in FIG. 1. The sensor in FIG. 4 includes an improved geometric arrangement for the cathode and anode.

The preferred embodiment of the electrical circuit 10 has two conductors 11 and 12 in the plurality. FIGS. 2, 3, and 4 show only two conductors 11 and 12 while the claims are directed to a plurality. Skilled artisans will appreciate that any number of conductors can be used since the claimed concept relates to the relative relationship of the distal end surfaces 13. Specifically, the facing distal end surfaces 13 wherein there are two conductors. 11 and 12 with stripped uninsulated wires that are substantially parallel to each other. Although parallel facing ends are not required, the ends should be adjacent to one another so that an electrochemical cell therebetween consumes the uninsulated wire thereof substantially from the distal end toward the proximal end. That was not the case in the known gas sensors.

To separate the cell from the blood stream while permitting measurement of in vivo gas the electrolyte 17 is contained within an oxygen gas permeable membrane 19 that permits oxygen to diffuse therethrough. In the preferred embodiment, FIG. 4, the cathode 20 is an insulated silver wire and the anode 21 is an insulated silver and/or silver chloride wire. Each wire is stripped of its polyester insulation near its respective distal end surface 13. The gas permeable membrane 19 is sized to fit within a catheter (not shown) of a diameter and length capable of being inserted into the vasculature of a human or animal.

An electrochemical cell results from the conductor wires, the electrolyte 17 in the gap 16 and the current sensitive measuring device in circuit with a power source 18 such as a battery between the proximal ends 14. The electrochemical cell is an oxygen sensitive device generating a current flow between one conductor wire, that is the anode 21 and another conductor wire, that is the cathode 20. The current is measurable at the proximal ends 14 which are conveniently outside the vasculature.

The preferred oxygen sensor can be carried in a protective sheath (not shown) having an overall diameter suitable for insertion through a catheter, for example, of 20 gauge that has been inserted into a port of the vasculature of a human or animal. In FIG. 4, the stripped cathode 20 has a shorter length than the length of the stripped anode 21. As shown in FIG. 4 the elongate anode is supported generally parallel to the cathode 20 and near the transition between the stripped portion and the insulated part of the anode 21 is folded into "U" shape 22 such that the distal end surface 13 thereof faces the distal end 13 of the cathode 21. While the figures show the insulation extends along anode 21 beyond the "U" shaped fold 22, that is not required so long as the distal end surface 13 of anode 21 is closer to the distal end surface 13 of cathode 20 as shown in FIG. 4.

A method for manufacturing an electrochemical sensor with the anode 21 and the cathode 20 begins with the step of folding near the transition between insulated part and the stripped portion of the anode 21 into the "U" shape 22 so that the uninsulated distal end surface 13 thereof faces in the direction of the proximal end thereof 14. The second step positions the cathode 20 adjacent the insulated part of the anode 21 with the uninsulated distal end surface 13 of the cathode 20 facing the distal end surface 13 of the anode 21 with the gap 16 therebetween. FIG. 4 shows the placement and configuration of the anode 21 and cathode 20 in the preferred embodiment. Placing the positioned cathode 20 and the facing anode 21 within the gas permeable membrane tube 19 with the anode 21 and cathode 20 parallel to an axis A, see FIG. 1 of the gas permeable membrane tube 19 is the next step in the preferred method. Sealing at 15 the insulated parts of the anode 21 and cathode 20 proximal the gap 16 provides an electrochemical cell chamber 23 within the gas permeable membrane tube 19. Although not disclosed herein the sealing can be with a compound as in the '888 patent mentioned in the background hereof or by melting the gas permeable membrane tube 19 to surround and support the conductors 11 and 12 in spaced parallel relation. Filling the gas permeable membrane tube 19 with electrolyte 17 to surround the facing distal end surfaces 13 is a further step. Closing the distal end of the gas permeable membrane tube 19 completes manufacture of the electrochemical cell.

What is claimed is:

1. An electrochemical sensor for the determination of the partial pressure of oxygen in a blood stream comprising a cathode and an anode immersed in an electrolyte contained in a chamber defined by an oxygen gas permeable membrane wherein each of the cathode and anode comprises the exposed uninsulated distal portion of a plurality of elongate insulated conductors each having an exposed uninsulated distal end surface and aproximal end; the elongate insulated conductors being associated with a support which positions each conductor with the insulated portions in parallel and the elongate conductor or conductors which form the anode is folded into a "U" shape so that the exposed distal end surface thereof faces the distal end surface of the cathode; the gap between the facing distal end surfaces of the cathode and anode being filled with an electrolyte to permit the flow of electric current across the gap; and the proximal end of each of the conductors is adapted to be connected to a current sensitive measuring device in circuit with a power source for monitoring changes in the flow of electric current between the distal end surfaces.

2. A sensor according to claim 1, wherein each of the cathode and anode comprises a single conductor.

3. A sensor according to claim 11, wherein the cathode is made of a noble metal wire and the anode is made of a silver and/or silver chloride wire.

4. A sensor according to claim 3, wherein the membrane is sized to fit within a catheter of a diameter and length sized to be inserted within the fasculature of a human or animal.

5. A sensor according to claim 5, wherein the cathode has a shorter length than the length of the anode.

6. A sensor according to claim 1, wherein the electrolyte is a buffered potassium chloride solution.

7. An electrical circuit for the in vivo monitoring of the partial pressure of oxygen in a patent's blood stream which comprises, in combination, an electrochemical sensor according to claim 1 connected, through the proximal end of each of the conductors, to a current sensitive measuring device in circuit with a power source, whereby changes in the flow of electric current between the distal end surfaces of the conductors may be monitored.

* * * * *